US010640539B2

(12) United States Patent
Vijaya et al.

(10) Patent No.: US 10,640,539 B2
(45) Date of Patent: May 5, 2020

(54) RECOMBINANT PROTEIN-BASED METHOD FOR THE DELIVERY OF SILENCER RNA TO TARGET THE BRAIN

(71) Applicant: Council of Scientific & Industrial Research, New Delhi (IN)

(72) Inventors: Gopal Vijaya, Hyderabad (IN); Ghulam Hassan Dar, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/278,319

(22) Filed: Feb. 18, 2019

(65) Prior Publication Data

US 2019/0309032 A1 Oct. 10, 2019

Related U.S. Application Data

(62) Division of application No. 15/266,642, filed on Sep. 15, 2016, now Pat. No. 10,208,098.

(51) Int. Cl.

| | | |
|---|---|---|
| *C07K 14/47* | (2006.01) | |
| *A61K 31/7105* | (2006.01) | |
| *C12N 15/87* | (2006.01) | |
| *C12N 15/11* | (2006.01) | |
| *A61K 47/64* | (2017.01) | |
| *A61K 31/713* | (2006.01) | |
| *C12N 15/113* | (2010.01) | |

(52) U.S. Cl.
CPC ............ *C07K 14/47* (2013.01); *A61K 31/713* (2013.01); *A61K 31/7105* (2013.01); *A61K 47/64* (2017.08); *C12N 15/111* (2013.01); *C12N 15/87* (2013.01); *C07K 2319/00* (2013.01); *C07K 2319/20* (2013.01); *C07K 2319/33* (2013.01); *C07K 2319/85* (2013.01); *C12N 15/1137* (2013.01); *C12N 2310/14* (2013.01); *C12N 2320/32* (2013.01); *C12Y 304/23046* (2013.01)

(58) Field of Classification Search
None
See application file for complete search history.

(56) References Cited

U.S. PATENT DOCUMENTS

| | | | | |
|---|---|---|---|---|
| 9,101,645 | B2* | 8/2015 | Watts ................. | A61K 31/12 |
| 9,193,969 | B2* | 11/2015 | Montefeltro ....... | A61K 49/0002 |
| 9,567,583 | B2* | 2/2017 | Yoon ................... | C12N 15/113 |
| 9,872,857 | B2* | 1/2018 | Tran ..................... | C12Q 1/6886 |
| 9,889,135 | B2* | 2/2018 | Koff ..................... | C12Q 1/6886 |
| 9,943,570 | B2* | 4/2018 | Androutsellis-Theotokis ............ | C12N 15/113 |
| 10,329,569 | B2* | 6/2019 | Kim .................. | C12N 15/1138 |
| 10,398,784 | B2* | 9/2019 | Mirkin .............. | A61K 47/6923 |
| 2006/0030003 | A1 | 2/2006 | Simon | |

OTHER PUBLICATIONS

K. Stojanov et al. "In Vivo Biodistribution of Prion- and GM1-Targeted Polymersomes following Intravenous Administration in Mice," Mol. Pharmaceutics, 9, 1620-1627, (2012).
S. Zhang et al. "Cationic lipids and polymers mediated vectors for delivery of siRNA," Journal of Controlled Release 123, 1-10, (2007).
V. Gopal "Bioinspired peptides as versatile nucleic acid delivery platforms," Journal of Controlled Release 167, 323-332, (2013).
P. Lonn et al., "Cationic PTD/CPP-mediated macromolecular delivery: charging into the cell", Expert Opin. Drug Deliv. 12 (10), (2015).
M. Serramia et al. "In vivo delivery of siRNA to the brain by carbosilane dendrimer," Journal of Controlled Release 200, 60-70, (2015).

(Continued)

*Primary Examiner* — Richard A Schnizer
(74) *Attorney, Agent, or Firm* — Locke Lord LLP; Nicholas J. DiCeglie, Jr.

(57) ABSTRACT

The present invention relates to the design and development of recombinant protein for the delivery of silencer RNA complex to mediate RNA interference since it represents a novel therapeutic approach to modulate several neurodegenerative disease-related genes across the blood-brain barrier (BBB). To overcome challenges due to this barrier for biologics and other biological complex, the present invention describes a method wherein peptide having sequence GGGGHLNILSTLWKYRC represented by SEQ ID NO. 1 known to target specific gangliosides was linked to a double-stranded RNA binding protein to bind and deliver silencer RNA to the brain parenchyma. The designed fusion protein comprising a double-stranded RNA-binding domain (dsRBD) of human Trans Activation response element (TAR) RNA Binding Protein (TARBP2) and a brain targeting peptide sequence that binds GM1. Conformation-specific binding of TARBP2 domain to silencer RNA results in the formation of homogenous serum-stable complex with GM1 targeting potential. Uptake of the complex in neural cells reveals selective requirement of GM1 for entry. Remarkably, the invention pertains to the systemic delivery of the complex comprising TARBP-BTP and silencer RNA in AβPP-PS1 mouse model of Alzheimer's disease (AD) led to distinctive localization primarily in the cerebral hemisphere in the hippocampus and brain cortex and in principle can work across other mammalian CNS targets. Further, the delivery of silencer-RNA mediated by brain targeting peptide fusion led to significant knockdown of BACE1, a therapeutic protease target in both AβPP-PS1 and wild type C57BL/6 mice. The invention establishes the emergent importance of fusion proteins in delivering therapeutic siRNA as a simple complex to brain tissues to treat neurodegenerative diseases besides Alzheimer's disease (AD). The complex is also useful to study gene function of hitherto unidentified genes/interplay of genes in mammalian systems and central nervous system.

2 Claims, 12 Drawing Sheets

Figure 1:
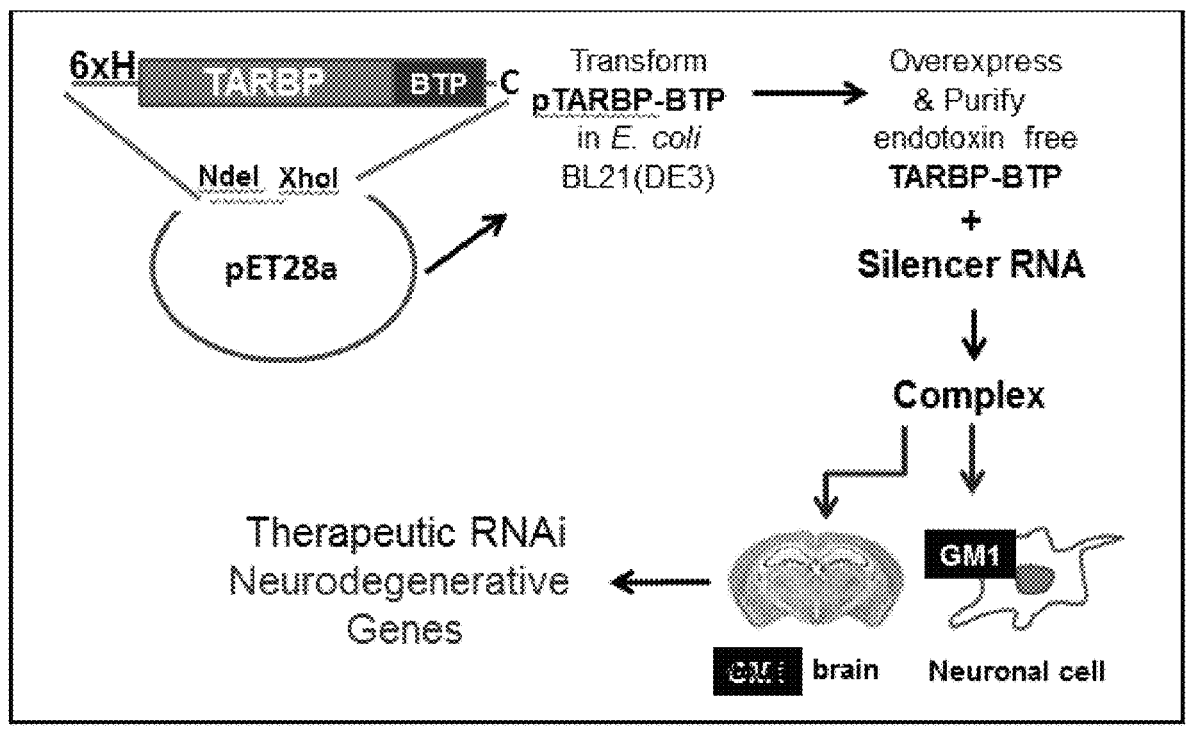
Figure 3A:
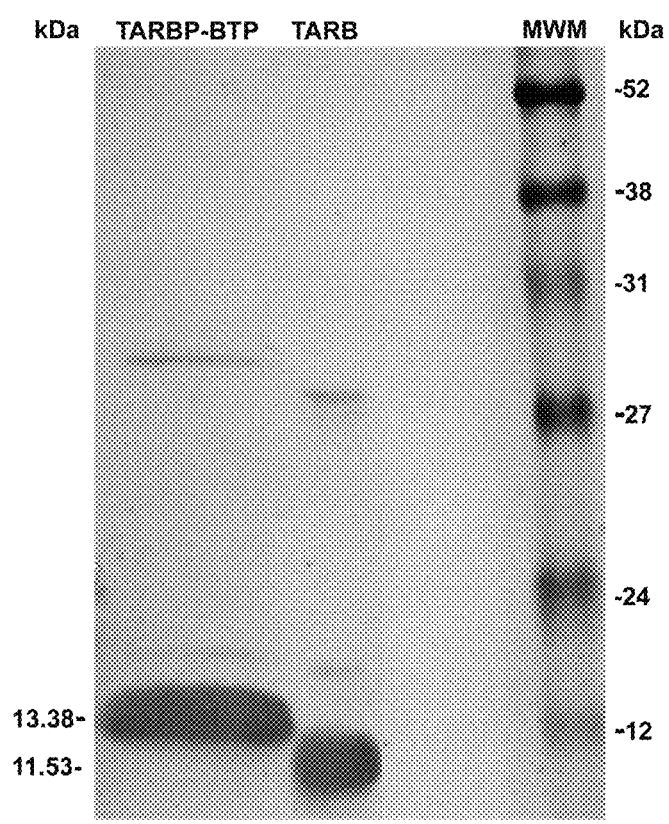
Figure 3B:
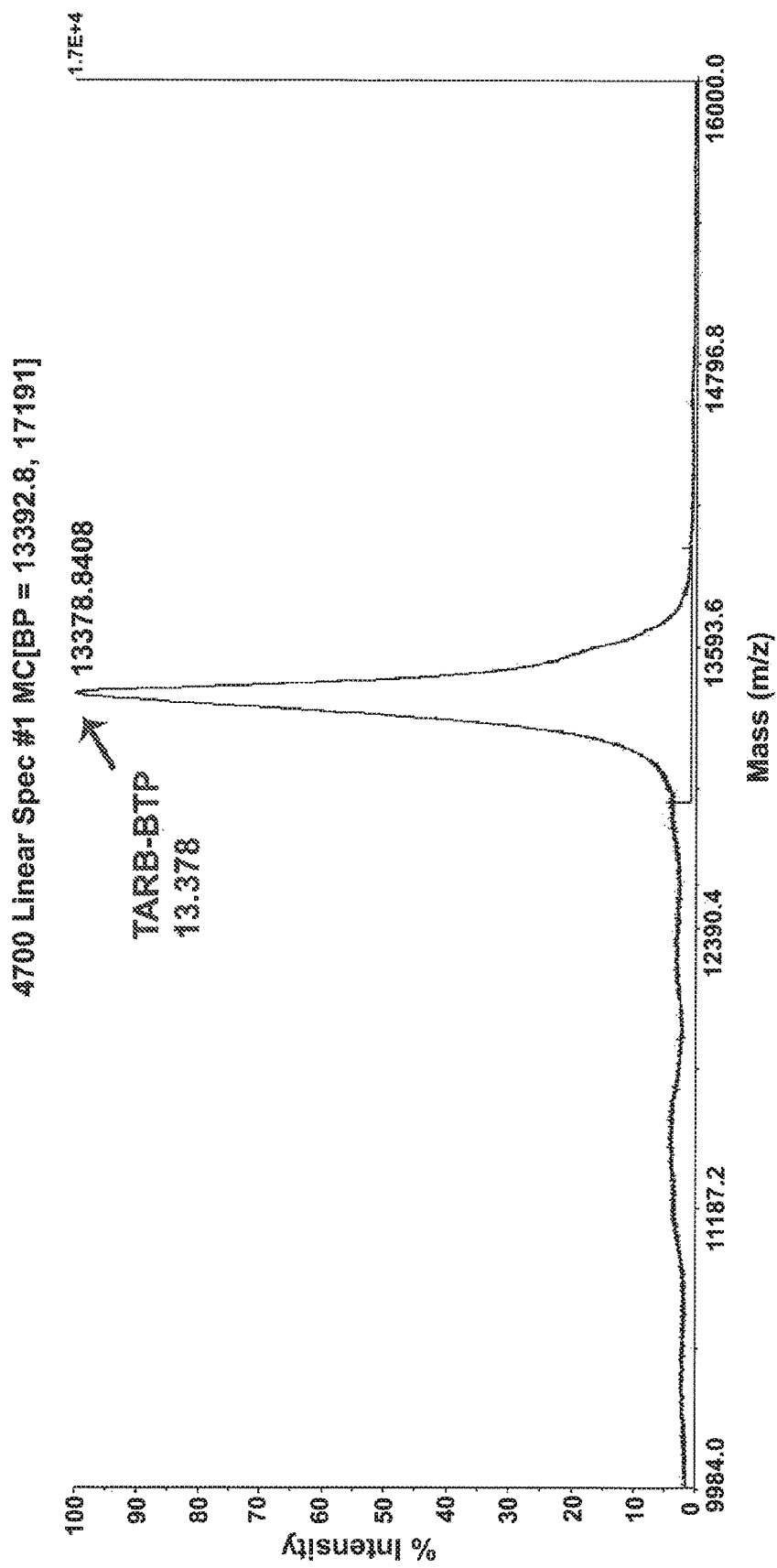
Figure 4:
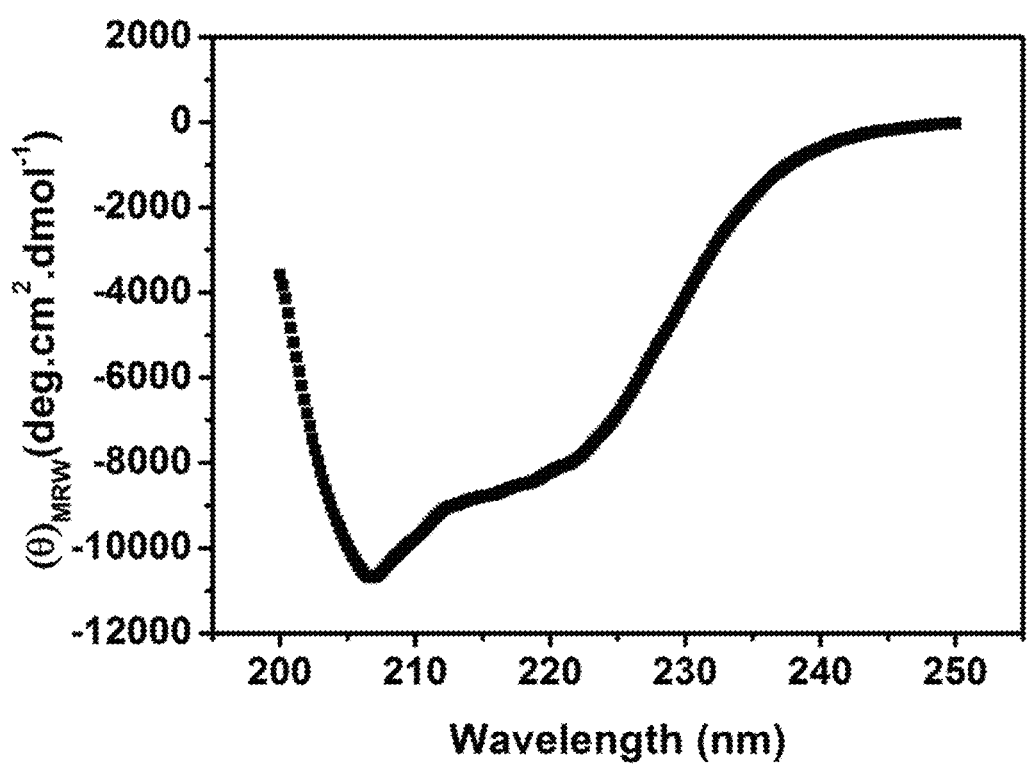
Figure 5:
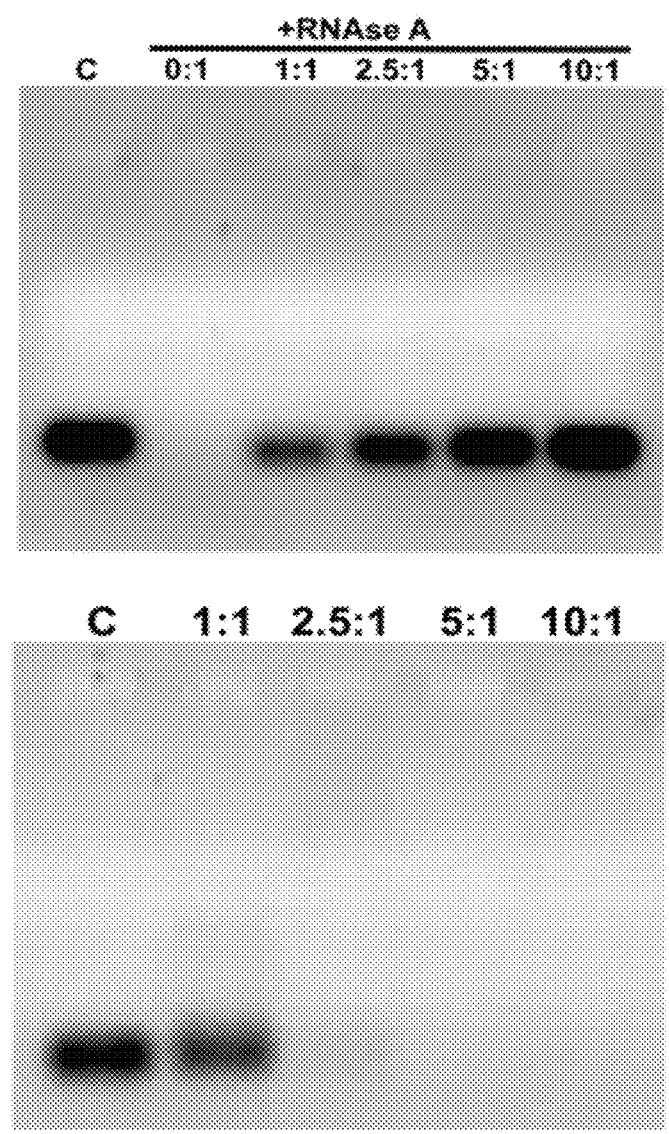
Figure 6:
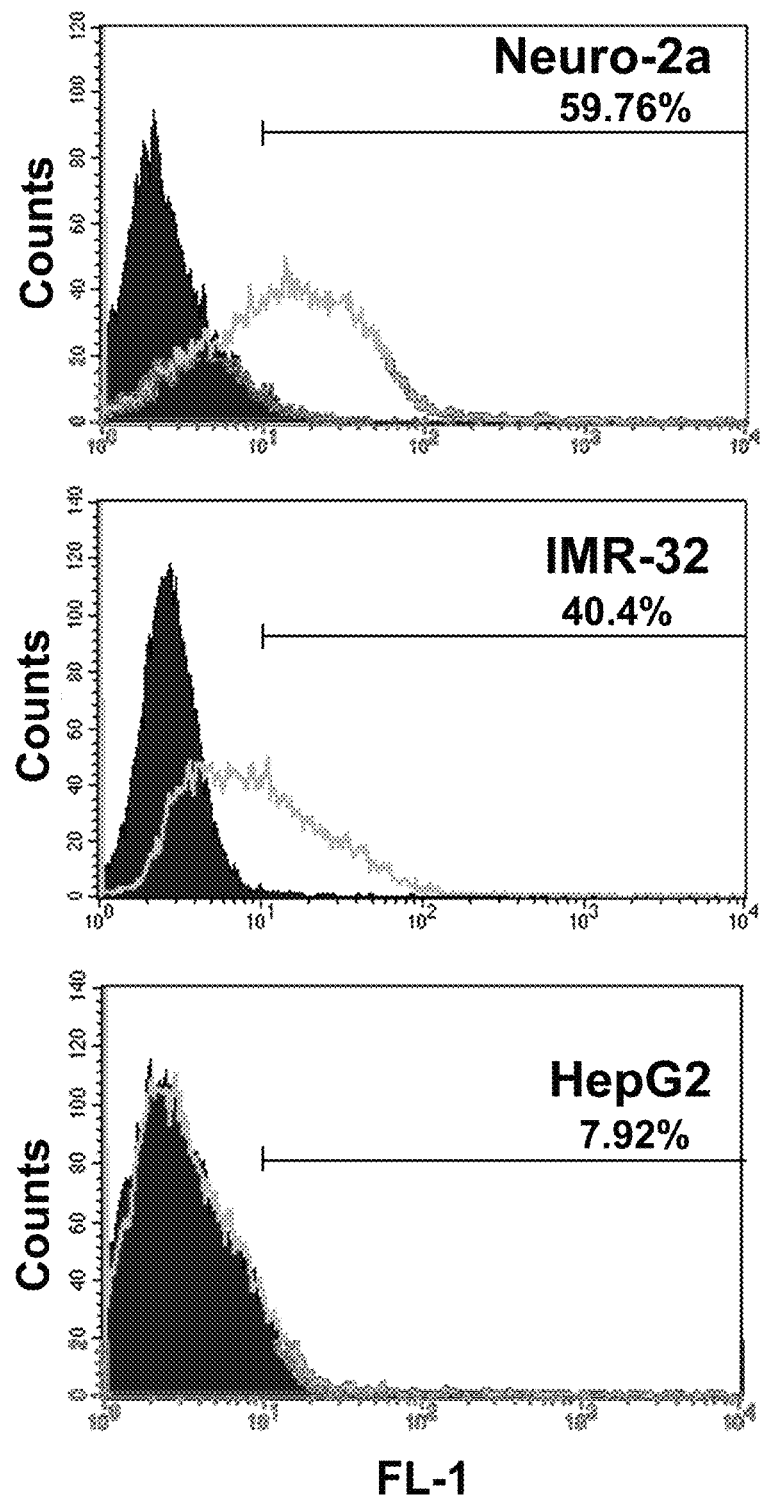
Figure 7:
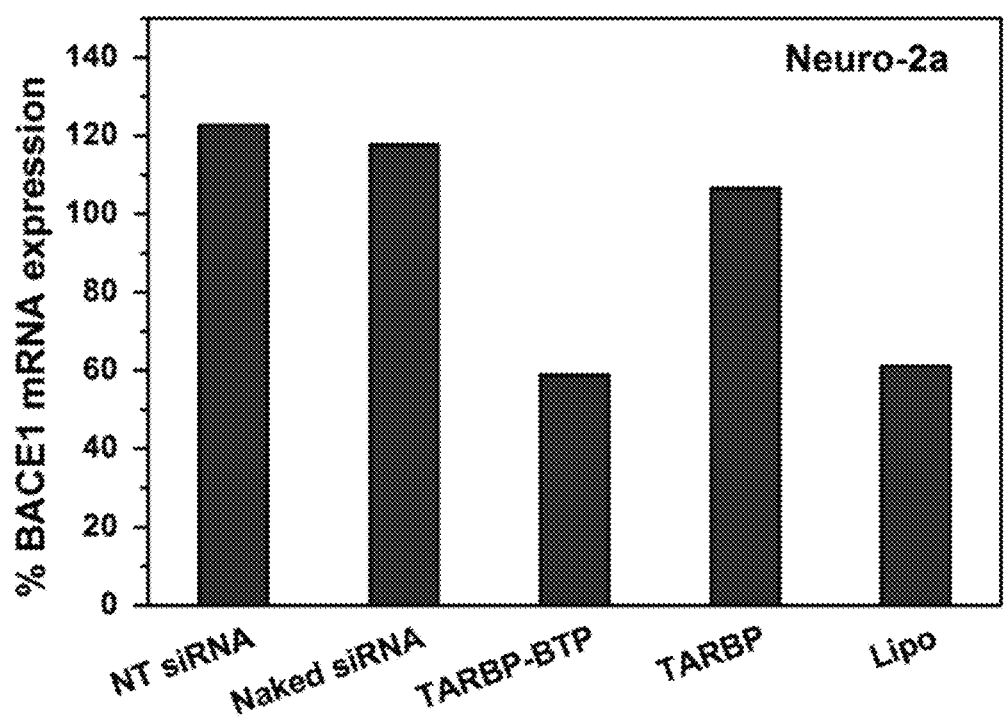
Figure 8:
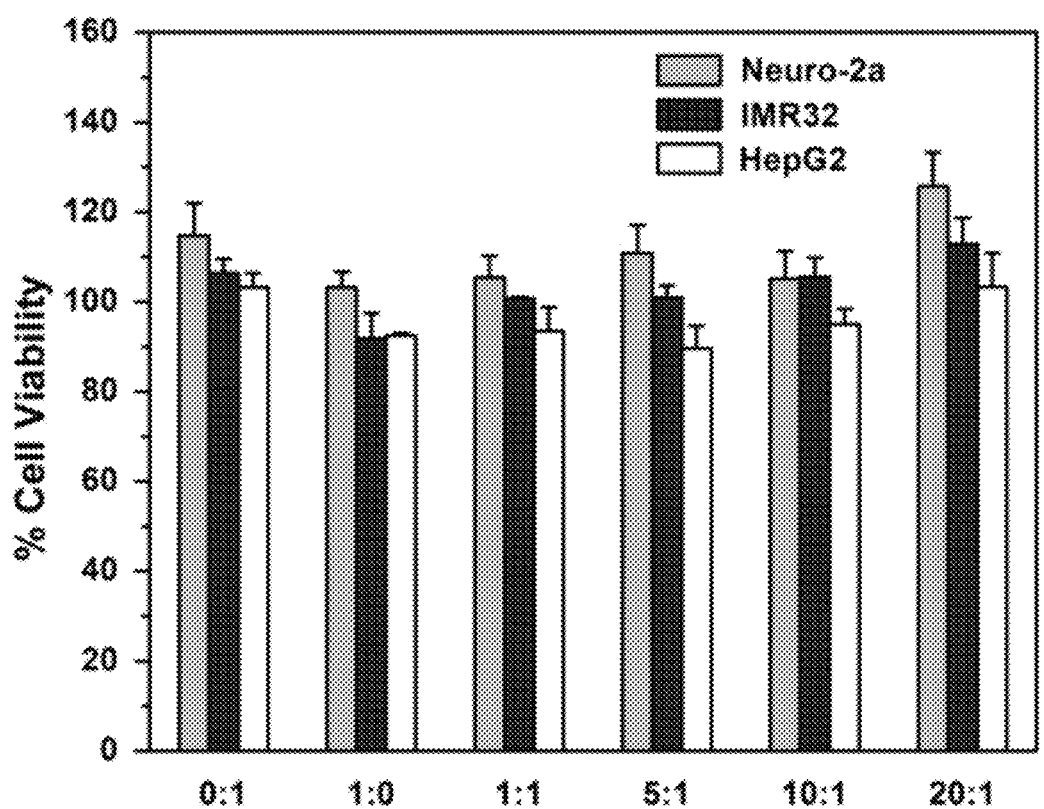
Figure 9:
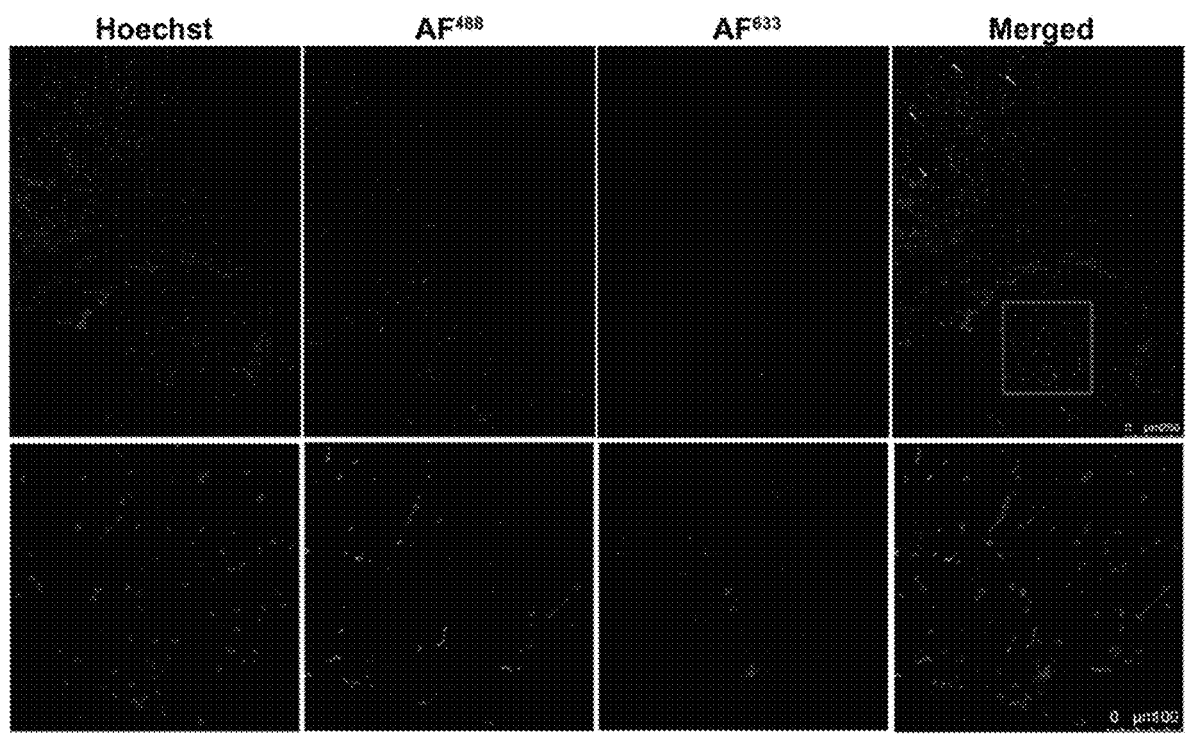

Specification includes a Sequence Listing.

(56) References Cited

OTHER PUBLICATIONS

M. Gooding et al., "siRNA Delivery: From Lipids to Cell-penetrating Peptides and Their Mimics," Chem Biol Drug Des 80, 787-809, (2012).
S. El Andaloussi et al., "Design of a peptide-based vector, PepFect6, for efficient delivery of siRNA in cell culture and systemically in vivo." Nucleic Acids Research, 39(9), 3972-3987, (2011).
M. M. Haroon et al., "A designed recombinant fusion protein for targeted delivery of siRNA to the mouse brain," Journal of Controlled Release 228, 120-131, (2016).
G. Hannon et al., "Unlocking the potential of the human genome with RNA interference," Nature, vol. 43, 371-378, (2004).
D. H. Kim et al., "RNAi mechanisms and applications," Biotechniques, 44(5), 613-616, (2008).
A. de Fougerolles et al., "Interfering with disease: a progress report on siRNA-based therapeutics," Nature Reviews—Drug Discovery 6, 443-456, (2007).
K. A. Whitehead et al., "Knocking down barriers: advances in siRNA delivery," Nature Reviews—Drug Discovery 8, 129-139, (2009).
M. A. Behlke "Chemical Modification of siRNAs for In Vivo Use," Oligonucleotides 18, 305-320, (2008).
J. T. Marques et al., "Activation of the mammalian immune system by siRNAs," Nature Biotechnology 23(11), 1399-1405, (2005).
M. Sioud et al., "Cationic liposome-mediated delivery of siRNAs in adult mice," Biochemical and Biophysical Research Communications 312, 1220-1225, (2003).
K. Kariko et al., "Small Interfering RNAs Mediate Sequence-Independent Gene Suppression and Induce Immune Activation by Signaling through Toll-Like Receptor 3," J. Immunol 172, 6545-6549, (2004).
N. Shi et al., "Noninvasive gene targeting to the brain," PNAS 97(13), 7567-7572 (2000).
W. M. Pardridge "Drug and Gene Targeting to the Brain with Molecular Trojan Horses," Nature Reviews—Drug Disclovery, vol. 1, 131-139, (2002).
D. Larocca et al., "Evolving Phage Vectors for Cell Targeted Gene Delivery," Current Pharmaceutical Biotechnology 3, 45-57, (2002).
J. V. Georgieva et al., "Peptide-Mediated Blood-Brain Barrier Transport of Polymersomes," Angew Chem. Int. Ed. 51, 1-5, (2012).
J. K. Liu et al., "A novel peptide defined through phage display for therapeutic protein and vector neuronal targeting," Neurobiology of Disease 19, 407-418, (2005).
R. J. Baodo et al., "Engineering and Expression of a Chimerica Transferrin Receptor Monoclonal Antibody for Blood-Brain Barrier Delivery in the Mouse," Biotechnol Bioeng. 102(4), 1251-1258, (2009).
P. Kumar et al., "Transvascular delivery of small interfering RNA to the central nervous system," Nature 448, 39-45, (2007).
B. Schneider et al., "Targeted siRNA Delivery and mRNA Knockdown Mediated by Bispecific Digoxigenin-binding Antiboides," Molecular Therapy—Nucleic Acids 1, 1-11, (2012).
B. A. Fiedel et al. "Complement activation by interaction of polyanions and polycations," Immunology 30, 161-169, (1976).
G. Hassan et al., "Conformation-dependent binding and tumor-targeted delivery of siRNA by a designed TRBP2: Affibody fusion protein," Nanomedicine, Nanotechnology, Biology, and medicine 11, 1455-1466, (2015).
S. Yamashita et al., "Structures of the first and second double-strnaded RNA-binding domains of human TAR RNA-binding protein," Protein Science 20, 118-130, (2011).
A. Eguchi et al., "Efficient siRNA Delivery into Primary Cells by Pepride Transduction-dsRNA Binding Domain (PTD-DRB) Fusion Protein," Nat Biotenchol. 27(6), 567-571, (2009).
H. A. Hansson et al., "Ultrastructural localization of cell membrane GM1 ganglioside by cholera toxin," Proc. Natl Acas. Sci. USA 74(9), 3782-3786, (1977).
S. Marconi et al., "Expression of gangliosides on glial and neuronal cells in normal and pathological adult human brain," Journal of Neuroimmunology 170, 115-121, (2005).
L. Alvarwz-Erviti et al., "Delivery of siRNA to the mouse brain by systemic injection of targeted exosomes," Nature Biotechnology 29(4), 341-347, (2011).
S. A. Lauer et al., "Development and Characterization of Ni-NTA-Bearing Microspheres," Cytometry 48, 136-145, (2002).
R. Rajagopalan et al., "Recombinant fusion proteins TAT-Mu, Mu and Mu-Mu mediate efficient non-viral gene delivery," The Journal of Gene Medicine 9, 275-286, (2007).
P. Reichelt et al., "Single Step protocol to purify recombinant proteins with low endotoxin contents," Protein Expression and Purification 46, 483-488, (2006).
Eguchi et al (Nature Biotechnology 27(6:567-572, 2009) (Year: 2009).
Liu et al (Molecular Therapy—Nucleic Acids (2014) 3, e162, 8 pages) (Year: 2014).
Haroon et al (J Contr Release 228: 120-131, Mar. 4, 2016).
Liu et al (Neurobiology of Disease 19 (2005) 407-418).
Park et al (J Gene Med 2007; 9: 691-702).
Dar et al (Supporting Information from Nanomedicine: Nanotechnology, Biology, and Medicine 11: 1455-1466,? ? Feb. 23, 2015)?
Singer et al (Nature Neuroscience 8(10:1343-1349, 2005).
Novagen pET System Manual 10th edition, Novagen, Inc. (May 2003).

* cited by examiner

To ORDER:
1)BTP: – GGC GGA GGT GGCCAT CTG AAC ATT CTG AGC ACC CTG TGG AAA TAT CGC TGC (SEQ ID NO: 6) synthetic primer for amplifying the brain targeting ligand
3) FBTP:5'– GCC CGG GAT GGC GGC GGA GGT GGCC-3' – 25 mer (SEQ ID NO: 7)
4) Rg-23: 5'-CTCGAGTTAGCAGCGATATTC-3'-22 mer (SEQ ID NO: 8)

SEQ ID NO: 7 and 8 are for overlap PCR of the targeting ligand

Sequencing data of samples submitted by Mohamed. Confirmed clone expressing TARBP-BTP Analyzed September 24th 2014
A05_Mohammed-2-T7 FOR.ab1 – confirmed TARBP-BTP
AGATGGCGGGTCATTCCCCTCTAGAATAATTTTGTTTAACTTTAAGAAGGAGATATACCATGGGCAGCAGCCA
TCATCATCATCATCACAGCAGCGGCCTGGTGCCGCGCGGCAGCCATATGGGCTCCCCTCAGCAGTCTGAGTGC
AACCCCGTTGGTGCTCTGCAGGAGCTGGTGGTGCAGAAAGGCTGGCGGTTGCCGGAGTACACAGTGACCCAGG
AGTCTGGGCCAGCCCACCGCAAAGAATTCACCATGACCTGTCGAGTGGAGCGTTTCATTGAGATTGGGAGTGG
CACTTCCAAAAAATTGGCAAAGCGGAATGCGGCGGCCAAAATGCTGCTTCGAGTGCACACGGTGCCTCTGGAT
GCCCGGGATGGCGGCGGAGGTGGCCATCTGAACATTCTGAGCACCCTGTGGAAATATCGCTGCTAACTCGAGC
ACCACCACCACCACCACTGAGATCCGGCTGCTAACAAAGCCCGAAAGGAAGCTGAGTTGGCTGCTGCCACCGC
TGAGCAATAACTAGCATAACCCCTTGGGGCCTCTAAACGGGTCTTGAGGGGTTTTTTGCTGAAAGGAGGAACT
ATATCCGGATTGGCGAATGGGACGCGCCCTGTAGCGGCGCATTAAGCGCGGCGGGTGTGGTGGTTACGCGCAG
CGTGACCGCTACACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTTTACGGCACCTCG
ACCCCAAAAAACTTGATTAGGGTGATGGTTCACGTAGTGGGCCATCGCCCTGATAGACGGTTTTTCGCCCTTT
GACGTTGGAGTCCACGTTCTTTAATAGTGGACTCTTGTTCCAAACTGGAACAACACTCAACCCTATCTCGGTC
TATTCTTTTGATTTATAAGGATTTTGCCGATTTCGGCCTATTGGTTAAAAAATGAGCTGATTAACAAAATTT
AACGCGAATTTAACAAATATTAACGCTTACAATTTAGTGCACTTTCGGGGAAATGTGCGCGGAACCCTATTTG
TTTATTTTTCTAAATACATCAATATGTATCCGCCTCATGATAGTCTAGAAAAACTCATCGAGCATCATTGACT
GCATTATTCATATCAGGATATCAATCCAAATTTTGGAAAGCGTTCTGTTATGAATGAAAAAACCTTCACCCGA
GGG    (SEQ ID NO: 17) Complete amplicon after cloning and transformation of TARBP-BTP cloned in pET 28a and then transformed in *Escherichia coli*
)
```
ID   VIRT31626                     Unreviewed;         123 AA.
AC   VIRT31626;
DE   Translation of nucleotide sequence generated on ExPASy
DE   on 24-Sep-2014 by 14.139.95.68.
CC   -!- This virtual protein sequence will automatically be deleted
CC       from the server after a few days.
DR   SWISS-2DPAGE; VIRT31626; VIRTUAL.
SQ   SEQUENCE   123 AA;  2103B34739E9046C CRC64.
     MGSSHHHHHHSSGLVPRGSHMGSPQQSECNPVGALQELVVQKGWRLPEYTVTQESGPAHR
     KEFTMTCRVERFIEIGSGTSKKLAKRNAAAKMLLRVHTVPLDARDGGGGGHLNILSTLWKYRC
```
   (SEQ ID NO: 16) translated sequence of gene amplified from *Escherichia coli*

Number of amino acids: 123 Molecular weight: 13558.4 Theoretical pI: 9.78
   Cloning sites NdeI and XhoI in bold

Fig. 2

Cloning strategy (Overlap PCR)
TRBP2-GGGGHLNILSTLWKYRC (SEQ ID NO: 9) Amino acid sequence of the targeting ligand linked to TRBP2 that can be expressed in *Escherichia coli*

Seq f TRBP2: real:
TCC CCT CAG CAG TCT GAG TGC AAC CCC GTT GGT GCT CTG CAG GAG CTG GTG GTG
CAG AAA GGC TGG CGG TTG CCG GAG TAC ACA GTG ACC CAG GAG TCT GGG CCA GCC
CAC CGC AAA GAA TTC ACC ATG ACC TGT CGA GTG GAG CGT TTC ATT GAG ATT GGG
AGT GGC ACT TCC AAA AAA TTG GCA AAG CGG AAT GCG GCG GCC AAA ATG CTG CTT
CGA GTG CAC ACG GTG CCT CTG GAT GCC CGG GAT GGC (SEQ ID NO: 11) Sequence corresponding to DNA originally isolated from HeLa Cells from which RNA was isolated and used to synthesize cDNA by reverse transcriptase as described in Supporting Information described for the construction of TRAF. (Dar et al. Nanomedicine (2015) Vol. 11 (1455-1466))
Organism Name : *Homo sapiens* TAR (HIV-1) RNA binding protein 2 (TARBP2), transcript variant 1, mRNA SPQQSEC NPVGALQELV VQKGWRLPEY TVTQESGPAH RKEFTMTCRV ERFIEIGSGT SKKLAKRNAA
AKMLLRVHTV PLDARDGGGG (SEQ ID NO: 12) Translated amino acid sequence obtained from SEQ No: 11

BTPprimer: cat ctg aac att ctg agc acc ctg tgg aaa tat cgc tgc (SEQ ID NO: 3) Synthetic primer designed for PCR Complete sequence of gene with Restriction sites (TRBP2-GGGGBTP)
CAT ATG GGC TCC CCT CAG CAG TCT GAG TGC AAC CCC GTT GGT GCT CTG CAG GAG
CTG GTG GTG CAG AAA GGC TGG CGG TTG CCG GAG TAC ACA GTG ACC CAG GAG TCT
GGG CCA GCC CAC CGC AAA GAA TTC ACC ATG ACC TGT CGA GTG GAG CGT TTC ATT
GAG ATT GGG AGT GGC ACT TCC AAA AAA TTG GCA AAG CGG AAT GCG GCG GCC AAA
ATG CTG CTT CGA GTG CAC ACG GTG CCT CTG GAT GCC CGG GAT GGC - GGC GGA GGT
GGC- CAT CTG AAC ATT CTG AGC ACC CTG TGG AAA TAT CGC TGC TAA CTC GAG
(restriction site) (SEQ ID NO: 13) Gene amplicon that can be generated in *Escherichia coli* after cloning and transformation.

N-terminus: NdeI– CAT ATG (SEQ ID NO: 14) restriction site NdeI created for cloning

C-terminus may: XhoI – CTC GAG (SEQ ID NO: 15) restriction site XhoI created for cloning

If put in pet 28a into the cloning sites, then final seq:
MGSSHHHHHH SSGLVPRGSH MGSPQQSECN PVGALQELVV QKGWRLPEYT VTQESGPAHR
KEFTMTCRVE RFIEIGSGTS KKLAKRNAAA KMLLRVHTVP LDARDG-GGGG HLNILSTLWKYRC
(SEQ ID NO: 16) 123 amino acids (MW-13.378kDa) Amino acid sequence corresponding to the molecular weight of TARBP-BTP.

STEP 1:
Fg23: GCCCGGGATGGCGGCGGAGGTGGCCAT (SEQ ID NO: 4)
Rg-23: CTCGAGTTAGCAGCGATATTT (SEQ ID NO: 5)

SEQ ID NO: 4 and 5 are designed forward and reverse synthetic primers

Fig. 2 (CONT...)

SEQUENCE LISTING

```
<160> NUMBER OF SEQ ID NOS: 17

<210> SEQ ID NO 1
<211> LENGTH: 5369
<212> TYPE: DNA
<213> ORGANISM: Escherichia coli

<400> SEQUENCE: 1
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttgt     180
cgacggagct cgaattcgga tccgcgaccc atttgctgtc caccagtcat gctagccata     240
tggctgccgc gcggcaccag gccgctgctg tgatgatgat gatgatggct gctgcccatg     300
gtatatctcc ttcttaaagt taaacaaaat tatttctaga ggggaattgt tatccgctca     360
caattcccct atagtgagtc gtattaattt cgcgggatcg agatctcgat cctctacgcc     420
ggacgcatcg tggccggcat caccggcgcc acaggtgcgg ttgctggcgc ctatatcgcc     480
gacatcaccg atggggaaga tcgggctcgc cacttcgggc tcatgagcgc ttgtttcggc     540
gtgggtatgg tggcaggccc cgtggccggg ggactgttgg gcgccatctc cttgcatgca     600
ccattccttg cggcggcggt gctcaacggc ctcaacctac tactgggctg cttcctaatg     660
```

-continued

```
caggagtcgc ataagggaga gcgtcgagat cccggacacc atcgaatggc gcaaaacctt    720
tcgcggtatg gcatgatagc gcccggaaga gagtcaattc agggtggtga atgtgaaacc    780
agtaacgtta tacgatgtcg cagagtatgc cggtgtctct tatcagaccg tttcccgcgt    840
ggtgaaccag gccagccacg tttctgcgaa aacgcgggaa aaagtggaag cggcgatggc    900
ggagctgaat tacattccca accgcgtggc acaacaactg gcgggcaaac agtcgttgct    960
gattggcgtt gccacctcca gtctggccct gcacgcgccg tcgcaaattg tcgcggcgat    1020
taaatctcgc gccgatcaac tgggtgccag cgtggtggtg tcgatggtag aacgaagcgg    1080
cgtcgaagcc tgtaaagcgg cggtgcacaa tcttctcgcg caacgcgtca gtgggctgat    1140
cattaactat ccgctggatg accaggatgc cattgctgtg gaagctgcct gcactaatgt    1200
tccggcgtta tttcttgatg tctctgacca gacacccatc aacagtatta ttttctccca    1260
tgaagacggt acgcgactgg gcgtggagca tctggtcgca ttgggtcacc agcaaatcgc    1320
gctgttagcg ggcccattaa gttctgtctc ggcgcgtctg cgtctggctg gctggcataa    1380
atatctcact cgcaatcaaa ttcagccgat agcggaacgg gaaggcgact ggagtgccat    1440
gtccggtttt caacaaacca tgcaaatgct gaatgagggc atcgttccca ctgcgatgct    1500
ggttgccaac gatcagatgg cgctgggcgc aatgcgcgcc attaccgagt ccgggctgcg    1560
cgttggtgcg gatatctcgg tagtgggata cgacgatacc gaagacagct catgttatat    1620
cccgccgtta accaccatca acaggatttt cgcctgctg gggcaaacca gcgtggaccg    1680
cttgctgcaa ctctctcagg gccaggcggt gaagggcaat cagctgttgc ccgtctcact    1740
ggtgaaaaga aaaaccaccc tggcgcccaa tacgcaaacc gcctctcccc gcgcgttggc    1800
cgattcatta atgcagctgg cacgacaggt ttcccgactg gaaagcgggc agtgagcgca    1860
acgcaattaa tgtaagttag ctcactcatt aggcaccggg atctcgaccg atgcccttga    1920
gagccttcaa cccagtcagc tccttccggt gggcgcgggg catgactatc gtcgccgcac    1980
ttatgactgt cttctttatc atgcaactcg taggacaggt gccggcagcg ctctgggtca    2040
ttttcggcga ggaccgcttt cgctggagcg cgacgatgat cggcctgtcg cttgcggtat    2100
tcggaatctt gcacgccctc gctcaagcct tcgtcactgg tcccgccacc aaacgtttcg    2160
gcgagaagca ggccattatc gccggcatgg cggccccacg ggtgcgcatg atcgtgctcc    2220
tgtcgttgag gacccggcta ggctggcggg gttgccttac tggttagcag aatgaatcac    2280
cgatacgcga gcgaacgtga agcgactgct gctgcaaaac gtctgcgacc tgagcaacaa    2340
catgaatggt cttcggtttc cgtgtttcgt aaagtctgga aacgcggaag tcagcgccct    2400
gcaccattat gttccggatc tgcatcgcag gatgctgctg gctaccctgt ggaacaccta    2460
catctgtatt aacgaagcgc tggcattgac cctgagtgat ttttctctgg tcccgccgca    2520
tccataccgc cagttgttta ccctcacaac gttccagtaa ccgggcatgt tcatcatcag    2580
taacccgtat cgtgagcatc ctctctcgtt tcatcggtat cattacccc atgaacagaa    2640
atcccctta cacggaggca tcagtgacca aacaggaaaa aaccgccctt aacatggccc    2700
gctttatcag aagccagaca ttaacgcttc tggagaaact caacgagctg gacgcggatg    2760
aacaggcaga catctgtgaa tcgcttcacg accacgctga tgagctttac cgcagctgcc    2820
tcgcgcgttt cggtgatgac ggtgaaaacc tctgacacat gcagctcccg gagacggtca    2880
cagcttgtct gtaagcggat gccgggagca gacaagcccg tcaggcgcg tcagcgggtg    2940
ttggcgggtg tcggggcgca gccatgaccc agtcacgtag cgatagcgga gtgtatactg    3000
```

```
gcttaactat gcggcatcag agcagattgt actgagagtg caccatatat gcggtgtgaa    3060
ataccgcaca gatgcgtaag gagaaaatac cgcatcaggc gctcttccgc ttcctcgctc    3120
actgactcgc tgcgctcggt cgttcggctg cggcgagcgg tatcagctca ctcaaaggcg    3180
gtaatacggt tatccacaga atcagggga t aacgcaggaa agaacatgtg agcaaaaggc    3240
cagcaaaagg ccaggaaccg taaaaaggcc gcgttgctgg cgttttt c ca taggctccgc    3300 cccc c tgacg agcatcacaa aaatcgacgc tcaagtcaga ggtggcgaaa cccgacagga    3360
ctataaagat accaggcgtt ccccctgga a gctccctcg tgcgctctcc tgttccgacc    3420
ctgccgctta ccggatacct gtccgccttt ctcccttcgg gaagcgtggc gctttctcat    3480
agctcacgct gtaggtatct cagttcggtg taggtcgttc gctccaagct gggctgtgtg    3540 cacgaaccc c ccgttcagcc cgaccgctgc gccttatccg gtaactatcg tcttgagtcc    3600
aacccggtaa gacacgactt atcgccactg gcagcagcca ctggtaacag gattagcaga    3660
gcgaggtatg taggcggtgc tacagagttc ttgaagtggt ggcctaacta cggctacact    3720
agaaggacag tatttggtat ctgcgctctg ctgaagccag ttaccttcgg aaaaagagtt    3780
ggtagctctt gatccggcaa acaaaccacc gctggtagcg gtggtttttt tgtttgcaag    3840
cagcagatta cgcgcagaaa aaaaggatct caagaagatc ctttgatctt ttctacgggg    3900
tctgacgctc agtggaacga aaactcacgt taagggattt tggtcatgaa caataaaact    3960
gtctgcttac ataaacagta atacaagggg tgttatgagc catattcaac gggaaacgtc    4020
ttgctctagg ccgcgattaa attccaacat ggatgctgat ttatatgggt ataaatgggc    4080
tcgcgataat gtcgggcaat caggtgcgac aatctatcga ttgtatggga agcccgatgc    4140
gccagagttg tttctgaaac atggcaaagg tagcgttgcc aatgatgtta cagatgagat    4200
ggtcagacta aactggctga cggaatttat gcctcttccg accatcaagc attttatccg    4260
tactcctgat gatgcatggt tactcaccac tgcgatcccc gggaaaacag cattccaggt    4320
attagaagaa tatcctgatt caggtgaaaa tattgttgat gcgctggcag tgttcctgcg    4380
ccggttgcat tcgattcctg tttgtaattg tcctttt a ac agcgatcgcg tatttcgtct    4440
cgctcaggcg caatcacgaa tgaataacgg tttggttgat gcgagtgatt ttgatgacga    4500
gcgtaatggc tggcctgttg aacaagtctg gaaagaaatg cataaacttt tgccattctc    4560
accggattca gtcgtcactc atggtgattt ctcacttgat aaccttattt ttgacgaggg    4620
gaaattaata ggttgtattg atgttggacg agtcggaatc gcagaccgat accaggatct    4680
tgccatccta tggaactgcc tcggtgagtt ttctccttca ttacagaaac ggctttttca    4740
aaaatatggt attgataatc ctgatatgaa taaattgcag tttcatttga tgctcgatga    4800
gtttttctaa gaattaattc atgagcggat acatatttga atgtatttag aaaaataaac    4860
aaataggggt tccgcgcaca tttccccgaa aagtgccacc tgaaattgta acgttaata    4920 ttttgttaaa attcgcgtta aattttgtt aaatcagctc attttttaac caataggccg    4980
aaatcggcaa aatcccttat aaatcaaaag aatagaccga gatagggttg agtgttgttc    5040
cagtttggaa caagagtcca ctattaaaga acgtggactc caacgtcaaa gggcgaaaaa    5100
ccgtctatca gggcgatggc ccactacgtg aaccatcacc ctaatcaagt tttttggggt    5160
cgaggtgccg taaagcacta atcggaacc c taaagggag ccccc gatt t agagcttgac    5220 ggggaaagcc ggcgaacgtg gcgagaaagg aagggaagaa agcgaaagga gcgggcgcta    5280
gggcgctggc aagtgtagcg gtcacgctgc gcgtaaccac cacacccgcc gcgcttaatg    5340
cgccgctaca gggcgcgtcc cattcgcca                                      5369
```

<210> SEQ ID NO 2
<211> LENGTH: 309
<212> TYPE: DNA
<213> ORGANISM: Escherichia coli

<400> SEQUENCE: 2

```
ggctcccctc agcagtctga gtgcaacccc gttggtgctc tgcaggagct ggtggtgcag      60
aaaggctggc ggttgccgga gtacacagtg acccaggagt ctgggccagc ccaccgcaaa     120
gaattcacca tgacctgtcg agtggagcgt tcattgaga ttgggagtgg cacttccaaa      180
aaattggcaa agcggaatgc ggcggccaaa atgctgcttc gagtgcacac ggtgcctctg     240
gatgcccggg atgcggcgg aggtggccat ctgaacattc tgagcaccct gtggaaatat     300
cgctgctaa                                                              309
```

<210> SEQ ID NO 3
<211> LENGTH: 39
<212> TYPE: DNA
<213> ORGANISM: Artificial Sequence
<220> FEATURE:
<223> OTHER INFORMATION: Synthetic primer designed for PCR

<400> SEQUENCE: 3

```
catctgaaca ttctgagcac cctgtggaaa tatcgctgc                              39
```

<210> SEQ ID NO 4
<211> LENGTH: 27
<212> TYPE: DNA
<213> ORGANISM: Artificial Sequence
<220> FEATURE:
<223> OTHER INFORMATION: Synthetic forward primer

<400> SEQUENCE: 4

```
gcccgggatg gcggcggagg tggccat                                           27
```

<210> SEQ ID NO 5
<211> LENGTH: 21
<212> TYPE: DNA
<213> ORGANISM: Artificial Sequence
<220> FEATURE:
<223> OTHER INFORMATION: Synthetic reverse primer

<400> SEQUENCE: 5

```
ctcgagttag cagcgatatt t                                                 21
```

<210> SEQ ID NO 6
<211> LENGTH: 51
<212> TYPE: DNA
<213> ORGANISM: Artificial Sequence
<220> FEATURE:
<223> OTHER INFORMATION: synthetic primer for amplifying the brain
      targeting ligand for expression in Escherichia coli

<400> SEQUENCE: 6

```
ggcggaggtg gccatctgaa cattctgagc accctgtgga aatatcgctg c                51
```

<210> SEQ ID NO 7
<211> LENGTH: 25
<212> TYPE: DNA
<213> ORGANISM: Artificial Sequence
<220> FEATURE:
<223> OTHER INFORMATION: Synthetic primer for overlap PCR

<400> SEQUENCE: 7

```
gcccgggatg gcggcggagg tggcc                                          25
```

<210> SEQ ID NO 8
<211> LENGTH: 22
<212> TYPE: DNA
<213> ORGANISM: Artificial Sequence
<220> FEATURE:
<223> OTHER INFORMATION: Synthetic primer for PCR

<400> SEQUENCE: 8

```
ctcgagttag cagcgatatt tc                                             22
```

<210> SEQ ID NO 9
<211> LENGTH: 17
<212> TYPE: PRT
<213> ORGANISM: Escherichia coli

<400> SEQUENCE: 9

```
Gly Gly Gly Gly His Leu Asn Ile Leu Ser Thr Leu Trp Lys Tyr Arg
 1               5                  10                  15

Cys
```

<210> SEQ ID NO 10
<211> LENGTH: 1888
<212> TYPE: DNA
<213> ORGANISM: Homo sapiens

<400> SEQUENCE: 10

```
gcctctccag ctgcgacaca gatggcgcgc gggctcttgg gttctgtagt tttctcgcga      60
tccaaaaggc tccgtgccca agtgagtcct taccgcctcc ctacccagcg gcttcccctc     120
cgctagtacg catgtccaca gcttcacgga ccgggagaga gggggcgcgg aaggaaggag     180
gcgggacggt attacaaaca aaaaaatacg gccttctcga aagcgacgg cggagggccc      240 gctcctccca gaaggcggtg cagcctgccc gggcagccag cgcacgcaga gggttgtggg     300
gcggatagct cccctccaga tggaggctca cgaagtaggg tgggcggggg actccatatc     360
ccagcgtgcc ccgcggcggg ccctaccggc gcgactccg ggcttggccc cggccctagc      420
tcgtcggctg tgtattgggg gcgcgtggagg ctgcagtcac ggtggcgccc gcggggacgg    480
aggagggaat gagtgaagag gagcaaggct ccggcactac cacgggctgc gggctgccta    540
gtatagagca aatgctggcc gccaacccag gcaagacccc gatcagcctt ctgcaggagt    600
atgggaccag aatagggaag acgcctgtgt acgaccttct caaagccgag gccaagccc     660 accagcctaa tttcaccttc cgggtcaccg ttggcgacac cagctgcact ggtcagggcc    720
ccagcaagaa ggcagccaag cacaaggcag ctgaggtggc cctcaaacac ctcaaagggg    780
ggagcatgct ggagccggcc ctggaggaca gcagttcttt ttctccccta gactcttcac    840
tgcctgagga cattccggtt tttactgctg cagcagctgc taccccagtt ccatctgtag    900
tcctaaccag gagccccccc atggaactgc agccccctgt ctcccctcag cagtctgagt    960
gcaaccccgt tggtgctctg caggagctgg tggtgcagaa aggctggcgg ttgccggagt   1020
acacagtgac ccaggagtct gggccagccc accgcaaaga attcaccatg acctgtcgag   1080
tggagcgttt cattgagatt gggagtggca cttccaaaaa attggcaaag cggaatgcgg    1140
cggccaaaat gctgcttcga gtgcacacgt tgcctctgga tgcccgggat ggcaatgagg   1200
tggagcctga tgatgaccac ttctccattg gtgtgggctc ccgcctggat ggtcttcgaa    1260
accgggggcc caggttgcac ctggattctc tacgaaattc agtaggagag aagatcctgt    1320
```

```
cctccgcag ttgctccctg ggctccctgg gtgccctggg ccctgcctgc tgccgtgtcc    1380
tcagtgagct ctctgaggag caggcctttc acgtcagcta cctggatatt gaggagctga    1440
gcctgagtgg actctgccag tgcctggtgg aactgtccac ccagccggcc actgtgtgtc    1500
atggctctgc aaccaccagg gaggcagccc gtggtgaggc tgcccgccgt gccctgcagt    1560
acctcaagat catggcaggc agcaagtgaa gccccagctg gactcatgga tgtgcaccct    1620
ttgctccctg ctctttctgc ctctgggctc atgtatctgc gcagctctgg taccctctgt    1680
gggtgccatc tctacctctg acacagactg cctgccttga agctgagaag cacagggca    1740 aggagccaag gaccagagag cctcagccag cccaggatcc gtcctcattt tattggtgat    1800
gatgaatggg aatgaaatca gggggctgtc tactagagcc tggaataaat atgctgcttt    1860
gtggattttt aaaaaaaaaa aaaaaaaa                                        1888

<210> SEQ ID NO 11
<211> LENGTH: 252
<212> TYPE: DNA
<213> ORGANISM: Homo sapiens

<400> SEQUENCE: 11
tcccctcagc agtctgagtg caaccccgtt ggtgctctgc aggagctggt ggtgcagaaa      60
ggctggcggt tgccggagta cacagtgacc caggagtctg gccagcccac cgcaaagaa     120 ttcaccatga cctgtcgagt ggagcgtttc attgagattg ggagtggcac ttccaaaaaa    180
ttggcaaagc ggaatgcggc ggccaaaatg ctgcttcgag tgcacacggt gcctctggat    240
gcccgggatg gc                                                         252

<210> SEQ ID NO 12
<211> LENGTH: 87
<212> TYPE: PRT
<213> ORGANISM: Homo sapiens

<400> SEQUENCE: 12

Ser Pro Gln Gln Ser Glu Cys Asn Pro Val Gly Ala Leu Gln Glu Leu
1               5                   10                  15

Val Val Gln Lys Gly Trp Arg Leu Pro Glu Tyr Thr Val Thr Gln Glu
                20                  25                  30

Ser Gly Pro Ala His Arg Lys Glu Phe Thr Met Thr Cys Arg Val Glu
        35                  40                  45

Arg Phe Ile Glu Ile Gly Ser Gly Thr Ser Lys Lys Leu Ala Lys Arg
    50                  55                  60

Asn Ala Ala Lys Met Leu Leu Arg Val His Thr Val Pro Leu Asp
65                  70                  75                  80

Ala Arg Asp Gly Gly Gly Gly
                85

<210> SEQ ID NO 13
<211> LENGTH: 321
<212> TYPE: DNA
<213> ORGANISM: Escherichia coli

<400> SEQUENCE: 13
catatgggct cccctcagca gtctgagtgc aaccccgttg gtgctctgca ggagctggtg      60
gtgcagaaag gctggcggtt gccggagtac acagtgaccc aggagtctgg ccagcccac     120 cgcaaagaat tcaccatgac ctgtcgagtg gagcgtttca ttgagattgg gagtggcact    180
```

```
tccaaaaaat tggcaaagcg gaatgcggcg gccaaaatgc tgcttcgagt gcacacggtg    240
cctctggatg cccgggatgg cggcggaggt ggccatctga acattctgag caccctgtgg    300
aaatatcgct gctaactcga g                                              321
```

<210> SEQ ID NO 14
<211> LENGTH: 6
<212> TYPE: DNA
<213> ORGANISM: Artificial Sequence
<220> FEATURE:
<223> OTHER INFORMATION: Restriction site NdeI created for cloning

<400> SEQUENCE: 14

```
catatg                                                                 6
```

<210> SEQ ID NO 15
<211> LENGTH: 6
<212> TYPE: DNA
<213> ORGANISM: Artificial Sequence
<220> FEATURE:
<223> OTHER INFORMATION: Restrictions site for XhoI created for cloning

<400> SEQUENCE: 15

```
ctcgag                                                                 6
```

<210> SEQ ID NO 16
<211> LENGTH: 123
<212> TYPE: PRT
<213> ORGANISM: Escherichia coli

<400> SEQUENCE: 16

```
Met Gly Ser Ser His His His His His His Ser Ser Gly Leu Val Pro
1               5                   10                  15

Arg Gly Ser His Met Gly Ser Pro Gln Gln Ser Glu Cys Asn Pro Val
            20                  25                  30

Gly Ala Leu Gln Glu Leu Val Val Gln Lys Gly Trp Arg Leu Pro Glu
        35                  40                  45

Tyr Thr Val Thr Gln Glu Ser Gly Pro Ala His Arg Lys Glu Phe Thr
    50                  55                  60

Met Thr Cys Arg Val Glu Arg Phe Ile Glu Ile Gly Ser Gly Thr Ser
65                  70                  75                  80

Lys Lys Leu Ala Lys Arg Asn Ala Ala Lys Met Leu Leu Arg Val
                85                  90                  95

His Thr Val Pro Leu Asp Ala Arg Asp Gly Gly Gly Gly His Leu
            100                 105                 110

Asn Ile Leu Ser Thr Leu Trp Lys Tyr Arg Cys
        115                 120
```

<210> SEQ ID NO 17
<211> LENGTH: 1244
<212> TYPE: DNA
<213> ORGANISM: Escherichia coli

<400> SEQUENCE: 17

```
agatggcggg tcattcccct ctagaataat tttgtttaac tttaagaagg agatatacca    60
tgggcagcag ccatcatcat catcatcaca gcagcggcct ggtgccgcgc ggcagccata   120
tgggctcccc tcagcagtct gagtgcaacc ccgttggtgc tctgcaggag ctggtggtgc   180 agaaggctg gcggttgccg gagtacacag tgacccagga gtctgggcca gcccaccgca   240
aagaattcac catgacctgt cgagtggagc gtttcattga gattgggagt ggcacttcca   300
```

-continued

```
aaaaattggc aaagcggaat gcggcggcca aaatgctgct tcgagtgcac acggtgcctc      360
tggatgcccg ggatggcggc ggaggtggcc atctgaacat tctgagcacc ctgtggaaat      420
atcgctgcta actcgagcac caccaccacc accactgaga tccggctgct aacaaagccc      480
gaaaggaagc tgagttggct gctgccaccg ctgagcaata actagcataa cccettgggg      540 cctctaaacg ggtcttgagg ggttttttgc tgaaaggagg aactatatcc ggattggcga      600
atgggacgcg ccctgtagcg gcgcattaag cgcggcgggt gtggtggtta cgcgcagcgt      660
gaccgctaca cttgccagcg ccctagcgcc cgctcctttc gctttcttcc cttcctttct      720
cgccacgttc gccggctttc cccgtcaagc tctaaatcgg gggctccctt tagggttccg      780
atttagtgct ttacggcacc tcgaccccaa aaaacttgat tagggtgatg gttcacgtag      840
tgggccatcg ccctgataga cggtttttcg ccctttgacg ttggagtcca cgttctttaa      900
tagtggactc ttgttccaaa ctggaacaac actcaaccct atctcggtct attcttttga      960
tttataagga ttttgccgat ttcggcctat tggttaaaaa atgagctgat taacaaaaat     1020
ttaacgcgaa tttaacaaat attaacgctt acaatttagt gcactttcgg ggaaatgtgc     1080
gcggaaccct atttgtttat ttttctaaat acatcaatat gtatccgcct catgatagtc     1140
tagaaaaact catcgagcat cattgactgc attattcata tcaggatatc aatccaaatt     1200
ttggaaagcg ttctgttatg aatgaaaaaa ccttcacccg aggg                      1244
```

RECOMBINANT PROTEIN-BASED METHOD FOR THE DELIVERY OF SILENCER RNA TO TARGET THE BRAIN

CROSS REFERENCE TO RELATED APPLICATIONS

This application is a Divisional of U.S. patent application Ser. No. 15/266,642 filed on Sep. 15, 2016, now U.S. Pat. No. 10,209,098, issued Feb. 19, 2019. The entire contents of this application is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 18, 2019, is named 0147NF2016_US-Div Sequence Listing_ST25.txt and is 17,150 bytes in size.

FIELD OF THE INVENTION

The present invention provides methods useful for the delivery of protein-based complex containing silencer RNA to target cells or tissues of the brain. The invention can be used to deliver pharmaceuticals to cross the blood-brain barrier in a non-invasive manner to deliver non-toxic biological complex to decrease levels of toxic substances generated in subjects leading to neurodegenerative diseases.

BACKGROUND OF THE INVENTION

Short interfering RNAs (siRNA) as gene-specific therapeutic molecules are resourceful tools to accurately control gene expression. However, delivery of these molecules to specific tissues is confronted due to their anionic nature, large size and non-specific effects preventing their clinical utility. Additionally, the delivery of siRNA to the brain parenchyma is restricted by the blood-brain barrier hampering treatment of subjects experiencing neurodegenerative conditions having long-term effects. To overcome these limitations while exploring for selectivity and non-toxicity, many peptide carriers were earlier established by conjugating antibody ligands and fusion proteins to nanoparticles through genetic engineering approaches, with the objective of targeting transferrin and insulin receptors of endothelial cells lining the brain capillaries. In a prominent advancement, different from these studies, numerous cell-targeting peptides were chosen through phage display by virtue of inherent tropism, increased avidity to mammalian cell surface receptors and ease of production. In an equivalent strategy, peptides with the binding characteristics of tetanus toxin to trisialoganglioside GT1b led to the discovery of a 12-aa peptide Tet1, offering the possibility of conjugating short peptides to larger protein scaffolds to generate multifunctional fusion proteins with neuronal tropism. Succeeding these studies, in a similar effort, Georgieva et al. developed strategies to conjugate neurotropic peptides to lipid-based molecules to impart in vivo stability, which demonstrated remarkable transcytotic capacity in vitro suggesting an identical mechanism in vivo. Upon systemic delivery, the targeting molecules, having affinity for GM1, were found to localize in the brain parenchyma and additionally in the lungs mandating further explorations to understand the potential of derivatized polymers displaying broad selectivity. Majority of non-viral vectors for nucleic acid delivery were earlier developed using the cationic lipids, cationic cell-penetrating peptides, and dendrimers. Spontaneous interaction of these molecules with nucleic acids led to the formation of stable non-covalent complexes. Knowledge-based rational design strategies subsequently led to the usage of multiple components for superior delivery and stability leading to successful target-specific gene silencing. Taking cues from neurotropic viruses, Kumar et al., fused the arginine peptide (9-mer) to a peptide derived from rabies virus glycoprotein (RVG) to facilitate electrostatic interaction with siRNA and specifically target acetylcholine receptors. The synthetic peptide fusion RVG-9R facilitated transvascular delivery of siRNA resulting in target specific gene silencing. However, presence of high density cationic charge on the carrier could lead to the formation of heterogeneous particles, non-specific biodistribution and lower yield of protein in suitable host systems.

RNA-recognition motifs conserved among double-stranded RNA-binding proteins lend their attributes to the design of modular fusion proteins. In a study using an arginine-rich peptide, tandem repeats of TAT was fused to the double-stranded RNA Binding Domain (DRBD) to electrostatically bind siRNA. The approach, although facilitating the delivery of siRNA into several primary cells including glioma lacked cell-specificity. It is thus evident that multiple DRBD motifs fused with cationic peptides may not confer additional in vivo advantage due to their likely interaction with serum proteins, lack of target selectivity and tendency to aggregate. Versatility of TARBP2 fusion protein whose conformation-dependent binding to double-stranded RNA abolished the prerequisite of positively charged peptides. The strong binding interactions led to the formation of neutral nanosized complex which were stable upon systemic administration. In the present invention, we have overcome the aforesaid barriers and invented a method to deliver siRNA selectively to target the brain and central nervous system, by fusing the RNA-binding domain with a peptide having sequence GGGGHLNILSTLWKYRC represented by SEQ ID NO. 9 that can retain flexibility and at the same time target GM1 and GT1b expressing cells, by virtue of their natural abundance of these receptors in neuronal cells to permit accumulation of the silencer complex with the aim of targeting disease causing genes in neurodegenerative condition by the advantage and ability of the peptide chimera to cross the blood-brain barrier by receptor-mediated transcytosis by mediating efficient and effective RNAi via GM1 in brain tissue.

OBJECTIVES OF THE INVENTION

The main objective of the present invention is to provide a method of preparation of a protein based complex comprising silencer RNA [siRNA] for target specific delivery to a ganglioside.

Another objective of the present invention is to provide a method for target specific delivery of a protein based complex comprising silencer RNA [siRNA] to a ganglioside.

Yet another objective of the present invention is to provide a protein based complex comprising silencer RNA [siRNA] for target specific delivery to a ganglioside by receptor mediated transcytosis.

An objective of the present invention is to provide a method of treating diseases selected from the group consisting of alzheimer's, parkinsons, gliomas, and amyotrophic lateral sclerosis which comprises administering to a subject an effective amount of protein based complex comprising silencer RNA [siRNA].

SUMMARY OF THE INVENTION

The present invention describes a method of preparation of a protein based complex comprising silencer RNA [siRNA] for target specific delivery to a ganglioside, wherein said method comprises:
a) fusing RNA Binding domain [RBD] of human Trans Activation Response Element RNA Binding Protein [TARBP] with a brain targeting peptide [BTP] to form a fusion protein [TARBP-BTP];
b) cloning, overexpressing and purifying said fusion protein [TARBP-BTP] to obtain a purified fusion protein [TARBP-BTP]; and
c) associating said purified fusion protein [TARBP-BTP] with siRNA to form a protein based complex.

In an embodiment of the present invention, the ganglioside is selected from GM1 or GT1b expressing cells.

In another embodiment of the present invention, RNA Binding domain is double stranded[dsRBD].

In a further embodiment of the present invention, TARBP-BTP protein and silencer RNA is mixed in 5:1 mole ratio.

In an embodiment of the present invention, TARBP-BTP protein and silencer RNA is mixed in 2.5:1 mole ratio.

In another embodiment of the present invention, silencer RNA is BACE1 silencer RNA.

In a further embodiment of the present invention, BTP is having amino acid sequence represented by SEQ ID NO. 9.

In an embodiment of the present invention, cloning is in pET28a plasmid, over expression in *E. coli* BL21(DE3) cells and purification using Ni-NTA affinity chromatography.

The present invention also describes a method for target specific delivery of a protein based complex comprising silencer RNA [siRNA] to a ganglioside, wherein said method comprises the steps of:

a) fusing RNA Binding domain [RBD] of human Trans Activation Response Element RNA Binding Protein [TARBP] with a brain targeting peptide [BTP] to form a fusion protein [TARBP-BTP];

b) cloning, overexpressing and purifying said fusion protein [TARBP-BTP] to obtain a purified fusion protein [TARBP-BTP];

c) associating said purified fusion protein [TARBP-BTP] with siRNA to form a protein based complex; and d) selectively targeting said protein based complex to the ganglioside by receptor mediated transcytosis.

In an embodiment of the present invention, ganglioside is selected from GM1 or GT1b expressing cells.

In another embodiment of the present invention, RNA Binding domain is double stranded [dsRBD].

In a further embodiment of the present invention, TARBP-BTP protein and silencer RNA is mixed in 5:1 mole ratio.

In an embodiment of the present invention, TARBP-BTP protein and silencer RNA is mixed in 2.5:1 mole ratio.

In another embodiment of the present invention, silencer RNA is BACE1 silencer RNA.

In a further embodiment of the present invention, BTP is having amino acid sequence represented by SEQ ID NO. 9.

In an embodiment of the present invention, cloning is in pET28a plasmid, over expression in *E. coli* BL21(DE3) cells and purification using Ni-NTA affinity chromatography.

The present invention describes a protein based complex comprising silencer RNA [siRNA] for target specific delivery to a ganglioside by receptor mediated transcytosis, wherein said complex comprises RNA Binding domain [RBD] of human Trans Activation Response Element RNA Binding Protein [TARBP] along with a brain targeting peptide [BTP] and silencer RNA.

The present invention also describes a method of treating diseases selected from the group consisting of alzheimer's, parkinsons, gliomas, and amyotrophic lateral sclerosis which comprises administering to a subject an effective amount of protein based complex comprising silencer RNA [siRNA].

These and other features, aspects, and advantages of the present subject matter will become better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE DRAWINGS

FIG. 1 is a schematic of the designed plasmid construct encoding TARBP-BTP and the overall method to target the brain.

FIG. 2 is a cloning strategy by overlap PCR and DNA sequencing.

FIG. 3 (A) is a SDS gel electrophoresis followed by Western blotting of purified TARBP-BTP (13.378 kDa) and TARBP (without the targeting peptide) 11.53 kDa. FIG. 3 (B) is a Matrix-assisted laser desorption ionization-time of flight mass spectrometry of TARBP-BTP. The major peak of the purified protein is 13.378 kDa.

FIG. 4 is a far-UV circular dichroism spectroscopy of TARBP-BTP.

FIG. 5 is depicting ability of complex to bind and protect silencer RNA (siRNA). Binding of the fusion protein to siRNA at 2.5:1 mole ratio with maximal binding at 5:1 mole ratio (bottom gel). At these ratios, the complex was resistant to degradation by RNase A and this ratio was used to prepare the functional complex for in vitro and in vivo experiments (top).

FIG. 6 depicts binding of TARBP-BTP complex with ganglioside GM1 which is internalized by cells in vitro. 59.76%, 40.4% and 7.92% of cells respectively were found to be FAM-positive clearly indicating that uptake is GM-1 dependent.

FIG. 7 depicts delivery of BACE1 silencer RNA in GM1-rich Neuro-2a cells. In vitro functional knockdown mediated by TARBP-BTP led to 41% knockdown of BACE1 mRNA levels.

FIG. 8 depicts evaluation of cell viability. Non-toxicity of the complex TARBP-BTP:siRNA at all the indicated ratios in vitro.

FIG. 9 depicts biodistribution of the complex in vivo upon intravenous delivery in AD mice. Localization of fluorescent complex is distinctly visible in the cerebral cortex and hippocampus (boxed area), which clearly indicates delivery of the complex by transcytosis across the blood-brain barrier.

FIG. 10 depicts therapeutic delivery of AD-relevant silencer complex in vivo in AD mice and C57BL/6 wild type mice mediated by TARBP-BTP:BACE1 mRNA levels of the different brain regions and organs were measured by qRT-PCR. a) 8-10 week old wild type C57BL/6 mice 48 h after i.v. injection with 20 nmol TARBP-BTP complexed with 4 nmol BACE1 siRNA (5:1 mole ratio) and compared with mice injected with complex containing 4 nmol siSTABLE non-targeting control siRNA #1 or 4 nmol naked BACE1 siRNA. b) BACE1 mRNA levels in organs of 8-10 week old wild type C57BL/6 mice injected with TARBP-BTP:BACE1 siRNA. c) BACE1 mRNA levels in 10-12 month AβPP-PS1 mice 48 h after i.v. injection with 20 nmol TARBP-BTP complexed with 4 nmol BACE1 siRNA (5:1 mole ratio). The values were normalized to respective PBS control (100%). β-Actin served as an internal control for all qRT-PCR experiments. d) Western blots of representative lysates from tissues obtained in (a and c) depict protein levels of the corresponding tissues. n=3 for each group. C=Control mice, T=Mice treated with TARBP-BTP:BACE1 siRNA complex. (* p<0.05 were considered statistically significant when compared to PBS control group. NS=not significant).

BRIEF DESCRIPTION OF THE SEQUENCE LISTING

SEQ ID NO: 1. pET28a Cloning vector (nucleic acid sequence)

SEQ ID NO: 2. TARBP-BTP nucleic acid sequence designed construct that can be expressed in *Escherichia coli* (nucleic acid sequence)

SEQ ID NO: 3. BTP Primer sequence: Synthetic primer designed for PCR (nucleic acid sequence)

SEQ ID NO: 4. Fg23 Primer sequence: Synthetic forward primer (nucleic acid sequence)

SEQ ID NO: 5. Rg 23 Primer sequence: Synthetic reverse primer (nucleic acid sequence)

SEQ ID NO: 6. BTP Primer sequence: synthetic primer for amplifying the brain targeting ligand for expression in *Escherichia coli* (nucleic acid sequence)

SEQ ID NO: 7. FBTP Primer sequence: Synthetic primer for overlap PCR (nucleic acid sequence)

SEQ ID NO: 8. Rg-23 Primer sequence: Synthetic primer for PCR (nucleic acid sequence)

SEQ ID NO: 9. BTP amino acid sequence of the targeting ligand linked to TRBP2 that can be expressed in *Escherichia coli* (amino acid sequence)

SEQ ID NO: 10. *Homo sapiens* TARBP2, RISC loading complex RNA binding subunit (TARBP2), transcript variant 1, mRNA (nucleic acid sequence)

SEQ ID NO: 11. fTRBP2: Sequence corresponding to DNA originally isolated from HeLa Cells from which RNA was isolated and used to synthesize cDNA by reverse transcriptase (nucleic acid sequence)

SEQ ID NO: 12. TARBP2 amino acid sequence: Translated amino acid sequence obtained from SEQ No: 11 (amino acid sequence)

SEQ ID NO: 13. Complete sequence of gene with Restriction site (TRBP2-CCCBTP): gene amplicon that can be generated in *Escherichia coli* after cloning and transformation (nucleic acid sequence)

SEQ ID NO: 14. NdeI Restriction site (nucleic acid sequence)

SEQ ID NO: 15. XhoI Restriction site (nucleic acid sequence)

SEQ ID NO: 16: TARBP-BTP complete amino acid sequence: translated amino acid sequence corresponding to the molecular weight of TARBP-BTP (amino acid sequence)

SEQ ID NO: 17. TARBP-BTP nucleotide sequence: complete amplicon after cloning and transformation of TARBP-BTP cloned in pET 28a and then transformed in *Escherichia coli* (nucleic acid sequence)

DETAILED DESCRIPTION OF THE INVENTION

The invention reveals the groundwork of the functional formulation that is a simple complex comprising of purified modular TARBP-BTP protein chimera with the brain targeting ligand. The chimera is an endotoxin-free protein molecule having the ability to form a consistent and active complex with short silencer RNA bound in a conformation-specific manner. The resultant complex containing TARBP-BTP containing the silencer RNA selectively targets GM1. The targeting functionality fosters the ability to cross the blood-brain barrier and localize in the brain tissues to mediate therapeutic RNA interference (RNAi). The invention established in a mouse model reveals that following non-invasive delivery, the complex is capable of entering and localizing in brain tissues particularly the hippocampus and the cortex and to some extent the olfactory bulb and the striatum and decrease levels of toxic peptide generation in these regions. These properties are the hallmark of a therapeutic pharmaceutical for treating neurodegenerative condition additionally in other mammalian subjects.

EXAMPLES

The following examples are given by way of illustration of the present invention and should not be construed to limit the scope of present disclosure. It is to be understood that both the foregoing general descriptions and the following detailed description are exemplary and explanatory only and are intended to provide further explanation of the subject matter.

Example 1

Design, Cloning Strategy by Overlap PCR and DNA Sequencing

To construct recombinant TARBP-BTP fusion, gene sequence from TRAF corresponding to the second domain (TARBP2/TRBP2) of the mammalian homolog, a linker sequence encoding five glycine residues and DNA fragment encoding the brain targeting peptide sequence together with a C-terminal cysteine codon was amplified by overlapping PCR. DNA duplexes with and without the targeting ligand were cloned in pET28a plasmid (Novagen) in the NdeI-XhoI site to generate N-terminal 6 His-tagged fusion constructs that were verified by DNA sequencing. The N-terminus-tagged fusion protein TARBP-BTP, a 13.378 kDa with the corresponding DNA and translated protein sequence by EXPASY. TARBP having high affinity to double-stranded RNA (dsRNA) was fused to a ganglioside targeting peptide sequence, originally selected by phage display for GT1b and GM1 binding to deliver siRNA to the brain.

Example 2

Purification and Verification of TARBP-BTP

The selected recombinants were expressed in *E. coli* BL21(DE3) cells and purified to homogeneity using Ni-NTA affinity chromatography. *E. coli* BL21(DE3) cells overexpressing the recombinant proteins were lysed under denaturing conditions using lysis buffer (50 mM sodium phosphate buffer pH 7.4 containing 300 mM NaCl, 10 mM Tris, 6 M urea and 1 mM PMSF) followed by sonication. Following centrifugation of the lysate at 18,000 rpm for 20 min to pellet cell debris, the supernatant was incubated with the pre-equilibrated Ni-NTA sepharose matrix for 1 h. The matrix was then loaded onto a column and washed with 0.1% Triton X-114 in lysis buffer at 4° C. to remove the bacterial endotoxins. The matrix bound TARBP-BTP protein was refolded under native conditions by on-column refolding and eluted using sodium phosphate buffer (pH 7.4) containing 300 mM imidazole. The eluted fractions were pooled, desalted and buffer exchanged in phosphate buffered saline (PBS) pH 7.4 using Sephadex G25 superfine column and purity and quality validated by western blotting and mass spectrometry.

Example 3

Far UV CD Spectrum

Far UV CD spectrum (range 250-200 nm) of purified TARBP-BTP (0.1 mg/ml in PBS (pH 7.4) recorded at room temperature using JASCO-J-815 spectropolarimeter equipped with Jasco Peltier-type temperature controller (CDF426S/15). The secondary structure analysis of TARBP-BTP by CD spectroscopy reveals that the secondary structure of the silencer-binding domain is unaltered. The spectrum, acquired in a 1 cm path length cuvette, was an average of five scans that was corrected for the buffer baseline and plotted using Origin? software (OriginLabCorp.). Spectra were recorded in ellipticity mode at a scan speed of 50 nm/min, response time of 2 s, bandwidth of 2 nm and data pitch of 0.2 nm. Mean residual ellipticity was calculated as described. Further, far-UV circular dichroism spectroscopy suggested a well-defined secondary structure, consisting of both α-helices and β-pleated sheets similar to earlier observations.

Example 4

Ability of Complex to Bind and Protect Silencer RNA (siRNA)

The complex was prepared by incubating 20 pmol of siRNA to increasing concentrations of TARB-BTP fusion protein in PBS buffer to obtain the preferred mole ratios and incubated for 20 min prior to electrophoresis. For the protection assay, the complex with and without the targeting ligand were incubated for 20 min followed by treatment with RNase A for 1 h at 37° C. Samples were then extracted by phenol:chloroform:isoamyl alcohol (25:24:1) and precipitated using ethanol as described previously and resolved by gel electrophoresis. The stability of TARBP-BTP and TARBP complex was further assessed by preparing the complex in PBS or DMEM media plus 10% serum followed by incubation for 1-6 h at 37° C. siRNA was then extracted by phenol-chloroform and resolved on 2% agarose gel and visualized by ethidium bromide staining. siRNA alone and TARBP-BTP or TARBP alone loaded in separate lanes serve as controls. Binding of the fusion protein to siRNA indicated strong association and formation of homogenous non-covalent complex that upon electrophoresis indicated strong binding and near-complete masking of siRNA at 2.5:1 mole ratio with maximal binding at 5:1 mole ratio. At these ratios, the complex was resistant to degradation by RNase A and this ratio was used to prepare the functional complex for the in vitro and in vivo experiments. Out data reflects the ability of recombinant his-tagged TARBP-BTP and his-tagged TARBP protein to bind dsRNA in a conformation-specific manner, an attribute essential for in vivo stability of the carrier upon delivery.

Example 5

TARBP-BTP Complex Binds Ganglioside GM1 and Internalized by Cells In Vitro

The complex was prepared at 5:1 mole ratio, since maximal binding and protection of siRNA was observed. Complex added to Neuro-2a, IMR32 and HepG2 cells in culture exhibiting varying levels of GM1 also depicted entry into cells via GM1 on the cell surface. This was supported in a FACS-based uptake assay evaluated in Neuro-2a, IMR32 and HepG2 cells using FAM-labeled siRNA complexed with TARBP-BTP. In such a condition, 59.76%, 40.4% and 7.92% of cells respectively were found to be FAM-positive clearly indicating that uptake is GM-1 dependent.

Example 6

In Vitro Functional Knockdown of TARBP-BTP:siRNA Complex

Delivery of BACE1 silencer RNA in GM1-rich Neuro-2a cells. Knockdown assay using qRT-PCR in Neuro-2a cells, having the highest levels of GM1 depicted that TARBP-BTP led to 41% knockdown of BACE1 mRNA levels.

Example 7

Non-Toxicity of the Complex TARBP-BTP:siRNA In Vitro

In the drawings accompanying the specification, the complex was non-toxic to cells when evaluated in an MTT cell-viability assay, which indicated ~90% viability at all the ratios examined. Cells were treated with TARBP-BTP:siRNA complex for 24 h and assessed in the presence and absence of siRNA at the indicated mole ratios using MTT. Cells treated with PBS alone were considered as controls having 100% viability from absorption values measured using reduced formazan. Error bars indicate standard deviation of triplicate sets.

Example 8

Biodistribution of the Complex In Vivo Upon Intravenous Delivery in AD Mice

Firstly, for the preparation of the protein complex comprising of silencer RNA and TARBP-BTP fusion protein was prepared in 1×PBS pH 7.4. The purified protein solution is then filtered using 0.22 mm Milex filters to get rid of any microbes and protein aggregates if any. The required amount of siRNA is also diluted in 1×PBS pH 7.4. Complexes are formed by mixing solutions of protein and siRNA in equal volumes eg. 100 ml of protein and 100 ml of siRNA (the concentrations are adjusted in such a way that the mole ratio is always kept at 5:1 protein:siRNA). Following the mixing, the solution is incubated at 4° C. for 15 min (incubation at RT may lead to the formation of aggregates). This complex (200 ml) is injected via the tail vein in mice using standard protocols of delivery. In the drawings accompanying the specification, the distribution of fluorescent complex (TARBP-BTP:siRNA) in AβPP-PS1 mouse brain upon intravenous delivery demonstrated its in vivo potential to cross the blood-brain barrier. This was executed by administering fluorescent complex that were prepared by mixing corresponding amounts of fluorescent-TARBP-BTP and silencer RNA at 5:1 mole ratio. Mice injected with the same volume of PBS served as negative controls. Mice were euthanized 6 h post-delivery of the complex and all the major organs, including brain were dissected, sectioned and visualized. Even though $AF^{633}$ signal originating from the labeled protein enabled collection of fluorescent signals in the far-red spectrum with minimum background noise, non-specific fluorescence arising from all laser lines in the brain sections was eliminated by $NaBH_4$ and $CuSO_4$ treatment of tissue sections as described in the methods. In the representative brain sections of mice injected with Alexa Fluor[633]-TARBP-BTP:siRNA complex, the localization of fluorescent complex is distinctly visible in the cerebral cortex and the hippocampus region (boxed area), which clearly indicates transcytosis of the complex across the blood-brain barrier. To authenticate that the observed signal arising from the 633 nm laser line is from the labeled protein, the emission spectrum was matched with that of AF[633]-TARBP-BTP fusion protein spotted separately on a coverslip, using lambda scan option in Leica SP8. In contrast, the lack of fluorescence in the lung, liver and intestine and other organs such as the heart and spleen indicated target specificity of TARBP-BTP. Fluorescence depicted in a different region of the brain i.e. brain cortex, is shown in Representative sections stained with CD31 mark the endothelial cells of the brain capillaries. Significant Alexa Fluor[633] fluorescence originating from kidney tissue sections indicated excretion of the labeled complex through renal filtration.

Example 9

Figure 10:
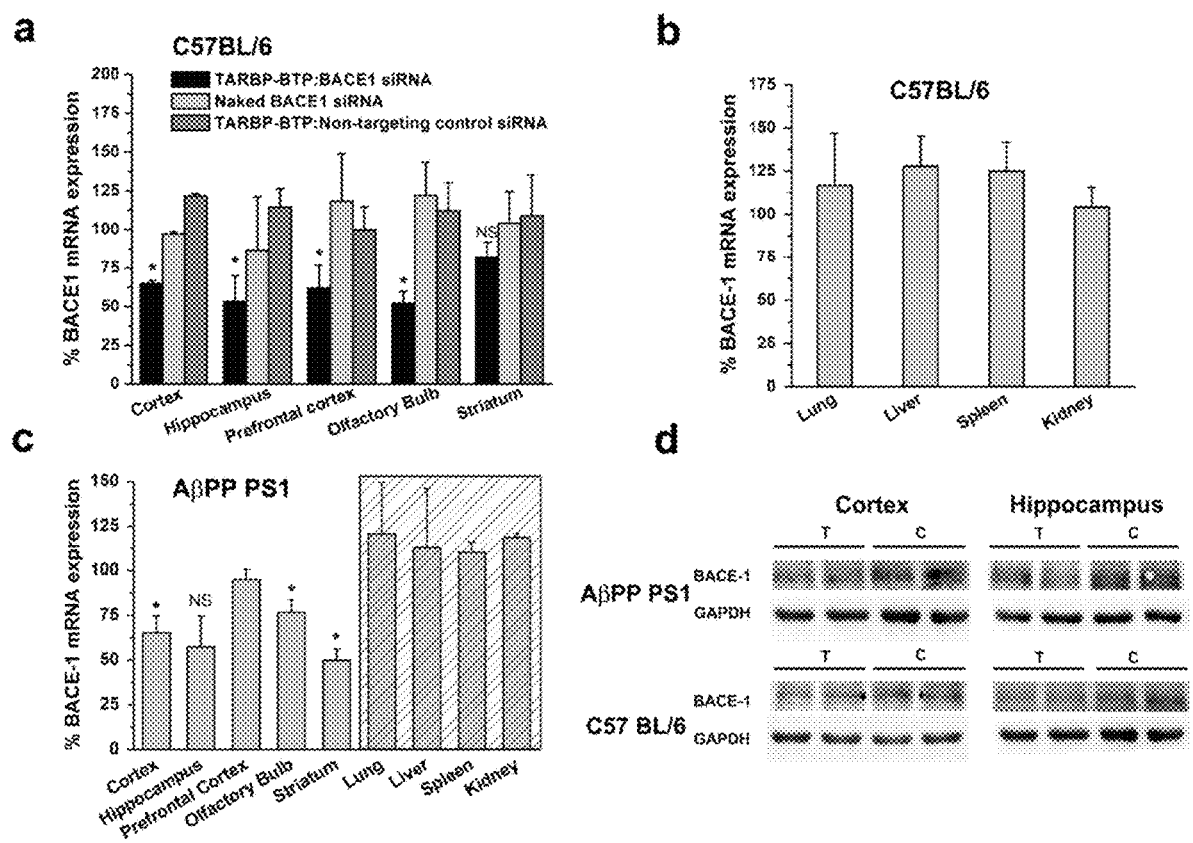

Therapeutic Delivery of AD-Relevant Silencer Complex In Vivo in AD Mice and C57BL/6 Wild Type Mice The role of BACE1 in the cleavage of amyloid precursor protein (APP) and consequent generation of Aβ peptide is known. Complex comprising TARBP-BTP and BACE1 silencer RNA at 5:1 mole ratio was intravenously delivered. Both AβPP-PS1 and C57BL/6 mice were injected with the complex intravenously and evaluated 48 h post administration by qRT-PCR and western blotting. In addition to PBS control, naked BACE1 silencer RNA and TARBP-BTP complexed with non-targeting control silencer RNA were also injected into C57BL/6 mice. FIG. 10 a-c demonstrates that a single dose delivered intravenously caused significant reduction in BACE1 mRNA levels amounting to 35%, 47%, 38% and 48% in the cortex, hippocampus, prefrontal cortex and olfactory bulb respectively in C57BL/6 mice. Reduction in BACE1 mRNA levels in AβPP-PS1 mice were 35%, 43%, 24% and 50% in the cortex, hippocampus, olfactory bulb and striatum respectively ($p<0.05$, except for hippocampus of AβPP-PS1 where $p=0.078$). The observed reduction in BACE1 mRNA levels evidently signifies the in vivo brain targeting potential of TARBP-BTP, an exceptional carrier of siRNA. Also, there were no changes in the BACE1 mRNA levels in liver, lung, kidney and spleen. Two additional controls i.e. naked BACE1 silencer RNA and non-targeting siRNA showed no significant changes in the BACE1 mRNA levels, which indicated that the observed reduction in BACE1 mRNA levels is significant.

ADVANTAGES OF THE INVENTION

In vivo experiments with BACE1 siRNA delivery mediated by TARBP-BTP clearly establish i) the in vivo stability, ii) tissue-specific targeting across the blood-brain barrier and prominently iii) region specificity of TARBP-BTP:siRNA complex in successfully delivering BACE1 validated silencer RNAs bound to the carrier complex. The functional complex comprising the bi-functional chimeric peptide and BACE1 silencer RNA, a therapeutically relevant AD gene, would be capable of mediating therapeutic effects by the ability to cross the blood-brain barrier and enter the brain tissues particularly in sites of learning and memory to knockdown expression of the products responsible for generating toxic peptides. The method is useful for targeting neurodegenerative diseases, e.g. AD and will find therapeutic applications in the central nervous system for other diseases.

Additionally, TARBP-BTP will be useful for functional analysis of hitherto unknown genes. The delivery system due to conformation-specific binding of the silencer offers a robust complex whose serum stability and controlled release in target tissues in a non-toxic and non-immunogenic manner will find utility in clinical applications.

We claim:

1. Protein based complex comprising silencer RNA (siRNA) for target specific delivery to a ganglioside by receptor mediated transcytosis, wherein said complex comprises RNA Binding domain (RBD) of human Trans Activation Response Element RNA Binding Protein (TARBP) along with a brain targeting peptide (BTP) and silencer RNA; and wherein said complex is prepared by a method which comprises:
   a) fusing a nucleic acid encoding a RNA binding domain (RBD) of human Trans Activation Response Element RNA Binding Protein (TARBP) with a nucleic acid encoding a brain targeting peptide (BTP) having the amino acid sequence of SEQ ID NO: 9 to form a TARBP-BTP fusion nucleic acid fusion construct encoding a TARBP-BTP fusion protein having the amino acid sequence of SEQ ID NO: 16;
   b) cloning the TARBP-BTP fusion nucleic acid fusion construct into an expression vector, overexpressing and purifying said TARBP-BTP fusion protein; and
   c) associating said purified TARBP-BTP fusion protein with an siRNA that targets the synthesis of a protein to form the protein based complex.

2. A method of treating diseases selected from the group consisting of Alzheimer's, Parkinson's, gliomas, and amyotrophic lateral sclerosis which comprises administering to a subject an effective amount of protein based complex comprising silencer RNA (siRNA) according to claim 1.

* * * * *